(12) United States Patent
Bonutti

(10) Patent No.: US 6,364,897 B1
(45) Date of Patent: *Apr. 2, 2002

(54) METHOD AND APPARATUS FOR POSITIONING A SUTURE ANCHOR

(76) Inventor: Peter M. Bonutti, 1303 W. Evergreen Plz., Effingham, IL (US) 62401

( * ) Notice: Subject to any disclaimer, the term of this patent is extended or adjusted under 35 U.S.C. 154(b) by 0 days.

This patent is subject to a terminal disclaimer.

(21) Appl. No.: 09/533,076

(22) Filed: Mar. 22, 2000

Related U.S. Application Data

(63) Continuation of application No. 09/084,627, filed on May 26, 1998, now Pat. No. 6,056,772, which is a division of application No. 08/764,199, filed on Dec. 13, 1996, now Pat. No. 5,814,073, and a continuation-in-part of application No. 08/470,142, filed on Jun. 6, 1995, and a continuation-in-part of application No. 08/467,002, filed on Jun. 6, 1995, now Pat. No. 5,674,240, and a continuation-in-part of application No. 08/254,368, filed on Jun. 6, 1994, now Pat. No. 5,573,517, and a division of application No. 08/013,942, filed on Feb. 4, 1993, now Pat. No. 5,320,611.

(51) Int. Cl.[7] ............................................. A61B 17/04
(52) U.S. Cl. ..................................................... 606/232
(58) Field of Search ........................... 606/232, 72, 73, 606/74, 104, 102, 139

(56) References Cited

U.S. PATENT DOCUMENTS

| | | |
|---|---|---|
| 319,296 A | 6/1885 | Molesworth |
| 668,879 A | 2/1901 | Miller |
| 702,789 A | 6/1902 | Gibson |
| 2,566,499 A | 9/1951 | Richter |
| 2,830,587 A | 4/1958 | Everett |
| 3,347,234 A | 10/1967 | Voss |
| 3,788,318 A | 1/1974 | Kim et al. |
| 3,789,852 A | 2/1974 | Kim et al. |
| 3,811,449 A | 5/1974 | Gravlee et al. |
| 3,833,003 A | 9/1974 | Taricco |

(List continued on next page.)

FOREIGN PATENT DOCUMENTS

SU 184396 7/1966

Primary Examiner—Gary Jackson
(74) Attorney, Agent, or Firm—Tarolli, Sundheim, Covell, Tummino & Szabo L.L.P.

(57) ABSTRACT

An inserter assembly is operable between a closed condition blocking movement of a suture anchor through the inserter assembly and an open condition in which the inserter assembly is ineffective to block movement of the anchor. The inserter assembly may have an end portion which pierces body tissue. In one embodiment, a tubular member has a plurality of segments which are moved from a closed condition to an open condition. In another embodiment, a plurality of wires extend along an inner side of a passage in a sheath. As the suture anchor slides along the wires, force is transmitted to the sheath to expand the sheath and operate the inserter assembly from the closed condition to the open condition. If desired, the wires may be omitted and the sheath resiliently expanded by a member which encloses the suture anchor. Indicia may be provided to indicate the depth to which the inserter assembly is inserted into body tissue.

22 Claims, 4 Drawing Sheets

U.S. PATENT DOCUMENTS

| | | |
|---|---|---|
| 3,968,800 A | 7/1976 | Vilasi |
| 4,183,102 A | 1/1980 | Guiset |
| 4,235,238 A | 11/1980 | Oglu et al. |
| 4,320,762 A | 3/1982 | Bentov |
| 4,461,281 A | 7/1984 | Carson |
| 4,504,268 A | 3/1985 | Herlitze |
| 4,589,868 A | 5/1986 | Dretler |
| 4,630,609 A | 12/1986 | Chin |
| 4,669,473 A * | 6/1987 | Richards et al. ............ 128/334 |
| 4,685,458 A | 8/1987 | Leckrone |
| 4,706,670 A | 11/1987 | Andersen et al. |
| 4,716,901 A | 1/1988 | Jackson et al. |
| 4,741,330 A | 5/1988 | Hayhurst |
| 4,846,812 A | 7/1989 | Walker et al. |
| 4,899,729 A | 2/1990 | Gill et al. |
| 4,921,479 A | 5/1990 | Grayzel |
| 4,954,126 A | 9/1990 | Wallsten |
| 4,966,583 A | 10/1990 | Debbas |
| 4,998,539 A | 3/1991 | Delsanti |
| 5,002,550 A | 3/1991 | Li |
| 5,021,059 A | 6/1991 | Kensey et al. |
| 5,037,404 A | 8/1991 | Gold et al. |
| 5,041,093 A | 8/1991 | Chu |
| 5,069,674 A | 12/1991 | Fearnot et al. |
| 5,183,464 A | 2/1993 | Dubrul et al. |
| 5,197,971 A | 3/1993 | Bonutti |
| 5,226,899 A | 7/1993 | Lee et al. |
| 5,234,425 A | 8/1993 | Fogarty et al. |
| 5,318,588 A | 6/1994 | Horzewski et al. |
| 5,320,611 A | 6/1994 | Bonutti et al. |
| 5,328,480 A | 7/1994 | Melker et al. |
| 5,354,302 A | 10/1994 | Ko |
| 5,395,308 A | 3/1995 | Fox et al. |
| 5,464,426 A | 11/1995 | Bonutti |
| 5,496,292 A | 3/1996 | Burnham |
| 5,522,846 A | 6/1996 | Bonutti |
| 5,549,630 A | 8/1996 | Bonutti |
| 5,681,352 A * | 10/1997 | Clancy, III et al. ......... 606/232 |
| 5,766,221 A * | 6/1998 | Benderev et al. ........... 606/232 |

* cited by examiner

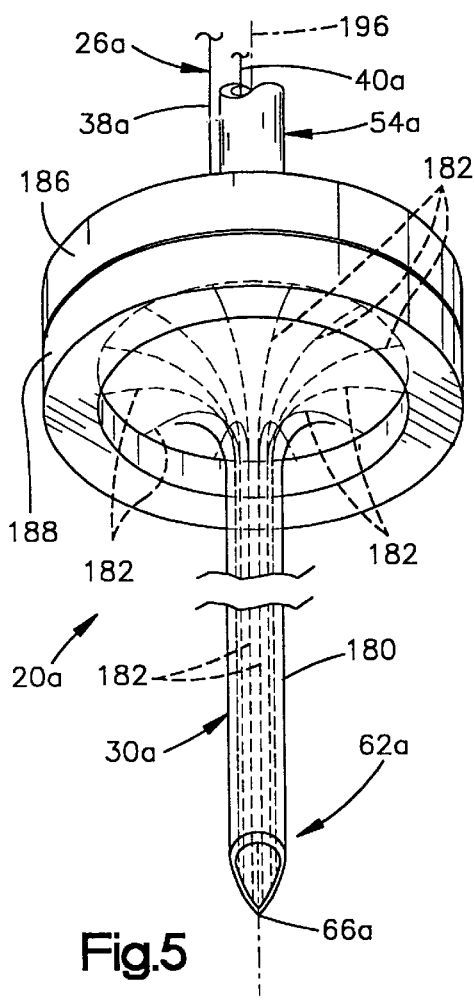
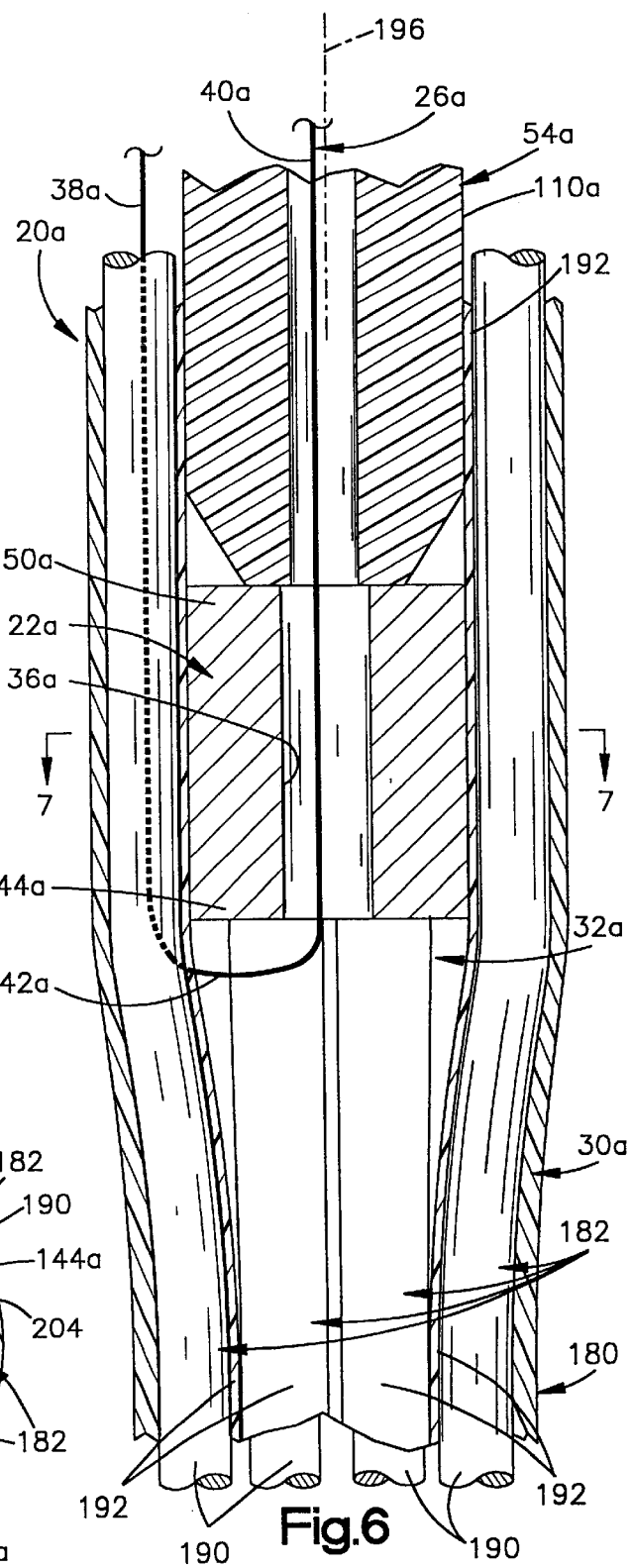
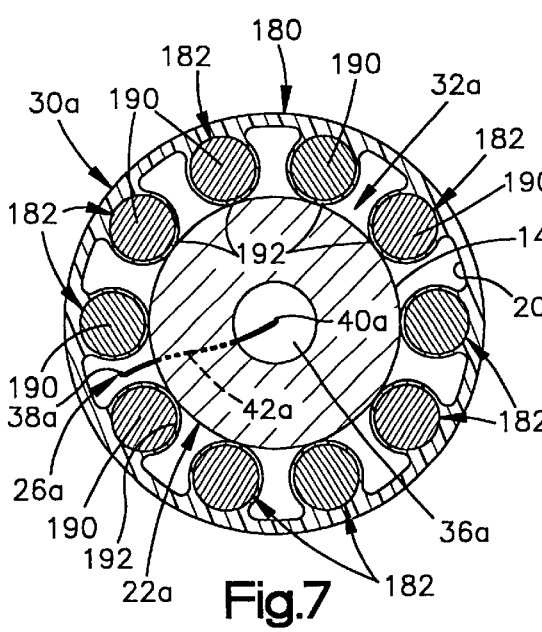

METHOD AND APPARATUS FOR POSITIONING A SUTURE ANCHOR

RELATED APPLICATIONS

This application is a continuation of U.S. patent application Ser. No. 09/084,627 filed May 26, 1998, now U.S. Pat. No. 6,056,772. The aforementioned application Ser. No. 09/084,627 is itself a divisional of U.S. patent application Ser. No. 08/764,199 filed Dec. 13, 1996, now U.S. Pat. No. 5,814,073. The aforementioned application Ser. No. 09/084,627 is also a continuation-in-part of U.S. patent application Ser. No. 08/470,142 filed Jun. 6, 1995. This application Ser. No. 08/470,142 is also a continuation-in-part of U.S. patent application Ser. No. 08/467,002 filed Jun. 6, 1995, now U.S. Pat. No. 5,674,240. The aforementioned applications Ser. Nos. 08/470,142 and 08/467,002 are themselves continuations-in-part of U.S. patent application Ser. No. 08/254,368 filed Jun. 6, 1994, now U.S. Pat. No. 5,573,517. The aforementioned application Ser. No. 08/254,368 is itself a divisional of U.S. patent application Ser. No. 08/013,942 filed Feb. 4, 1993, now U.S. Pat. No. 5,320,611. The benefit of the earlier filing dates of all of the aforementioned U.S. patent applications is hereby claimed for all subject matter common to this application and any of the aforementioned applications.

BACKGROUND OF THE INVENTION

The present invention provides a new and improved apparatus and method for use in positioning a suture anchor in either soft or hard body tissue.

Surgeons utilize suture anchor inserters to position suture anchors in either soft body tissue or hard body tissue. Suture anchor inserters for positioning suture anchors in soft or hard body tissue are disclosed in U.S. Pat. Nos. 5,403,348; 5,464,426; and 5,549,630. During positioning of a suture anchor relative to body tissue, it is necessary to form an opening in the body tissue to receive the anchor. In addition, during positioning of the suture anchor relative to the body tissue, it is advantageous to be able to accurately position the anchor in a desired depth in the body tissue.

SUMMARY OF THE INVENTION

An apparatus which may be used to position a suture anchor relative to body tissue includes a tubular member. The tubular member is advantageously operable between a closed condition at least partially blocking a passage in the tubular member and an open condition in which the tubular member is ineffective to block the passage. By blocking the passage in the tubular member, entry of body tissue and/or other foreign matter into the passage is prevented.

In some embodiments of the invention, when the tubular member is in the closed condition, the leading end portion of the tubular member is contracted so as to be readily inserted into body tissue. A point at the contracted end of the tubular member facilitates piercing of body tissue.

Upon movement of a suture anchor through the end portion of the tubular member, a leading end portion of the anchor may apply force against the tubular member to effect operation of the tubular member from the closed condition to the open condition. Alternatively, a second member may be inserted into the tubular member along with the suture anchor. The second member applies force against an inner side surface of the tubular member to effect operation of the tubular member from the closed condition to the open condition.

In one specific embodiment of the invention, the tubular member includes a sheath which encloses a plurality of wires. A leading end portion of the sheath may be expanded by applying force against the wires with the anchor. A portion of the suture may be disposed between the wires.

Indicia may be provided on the outside of the tubular member to indicate the depth to which the tubular member has been inserted into body tissue. When indicia corresponding to a desired depth of insertion of the tubular member in the body tissue has been covered by the body tissue, the step of inserting the tubular member into body tissue is interrupted.

BRIEF DESCRIPTION OF THE DRAWINGS

The foregoing and other features of the present invention will become more apparent upon the consideration of the following description taken in connection with the accompanying drawings, wherein:

FIG. 5 is a simplified schematic pictorial illustration of a second embodiment of the inserter assembly, a pointed leading end portion of the inserter assembly being illustrated in a closed condition;

FIG. 6 is an enlarged simplified schematic sectional view of a portion of the inserter assembly of FIG. 5 and illustrating the manner in which a suture anchor is moved along and expands a passage in the inserter assembly;

FIG. 7 is a sectional view, taken generally along the line 7—7 of FIG. 6, illustrating the manner in which the suture anchor engages wires enclosed by a sheath of the inserter assembly;

DESCRIPTION OF SPECIFIC PREFERRED EMBODIMENTS OF THE INVENTION

General Description

Figure 1:
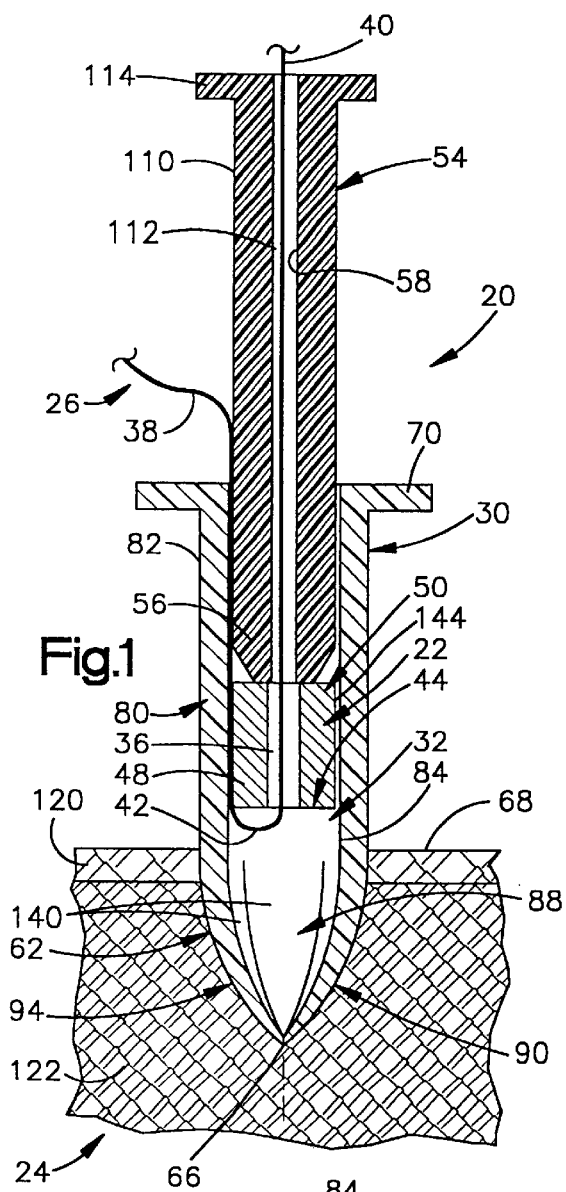
FIG. 1 is an enlarged simplified schematic illustration of a suture anchor inserter assembly which is constructed in accordance with the present invention and includes a tubular member having a pointed leading end portion which is illustrated in a closed condition.

An inserter assembly 20 (FIG. 1) is used to position a suture anchor 22 relative to body tissue 24. During positioning of the suture anchor 22 relative to the body tissue 24, a suture 26 engages the suture anchor 22. Once the suture anchor 22 has been positioned in the body tissue 24, the suture anchor holds the suture 26 against pulling out of the body tissue.

The inserter assembly 20 includes a tubular outer member 30. The tubular outer member 30 has a passage 32 through which the suture anchor 22 moves into the body tissue 24. The suture anchor 22 has a passage 36 through which the suture 26 extends. The suture 26 includes an outer leg or portion 38 which extends along an outer side of the suture anchor 22 and an inner leg or portion 40 which extends through the passage 36 in the suture anchor 22. A connector portion 42 of the suture extends across an annular leading end portion 44 of the suture anchor 22.

In the embodiment of the suture anchor 22 illustrated in FIG. 1, the suture 26 extends through the passage 36 disposed in the suture anchor. However, it is contemplated that the suture 26 could be connected with the suture anchor 22 in a different manner. For example, the suture 26 could be tied off at an opening in the suture anchor 22 if desired.

The illustrated suture anchor 22 has a cylindrical tubular side wall 48 which extends between the leading end portion 44 and an annular trailing end portion 50 of the suture anchor 22. It should be understood that the suture anchor 22 could have a different configuration. For example, the suture anchor 22 could have a polygonal configuration which is similar to the polygonal configuration of a suture anchor disclosed in U.S. Pat. No. 5,549,630 issued Aug. 27, 1996 to Peter M. Bonutti. Alternatively, the suture anchor 22 could have any one of the configurations disclosed in U.S. Pat. No. 5,522,846 issued Jun. 4, 1996 to Peter M. Bonutti.

The suture anchor 22 is formed of metal. Specifically, the suture anchor 22 is formed of stainless steel. However, it is contemplated that the suture anchor 22 could be formed of other materials, for example, body tissue. Alternatively, the suture anchor 22 could be formed of a polymeric material such as cellulose, petroylglutamic acid, collagen, or polylactide. If desired, the suture anchor 22 could be formed of a material which is hydrophilic and expands when exposed to body fluids.

A tubular inner or pusher member 54 is telescopically received in the tubular outer member 30. The tubular inner member 54 has a leading end portion 56 which engages the trailing end portion 50 of the suture anchor 22. The inner leg 40 of the suture 26 extends through a passage 58 in the tubular inner member 54. The tubular inner member 54 is movable axially along the passage 32 in the tubular outer member 30 to push the suture anchor 22 into body tissue.

Figure 4:
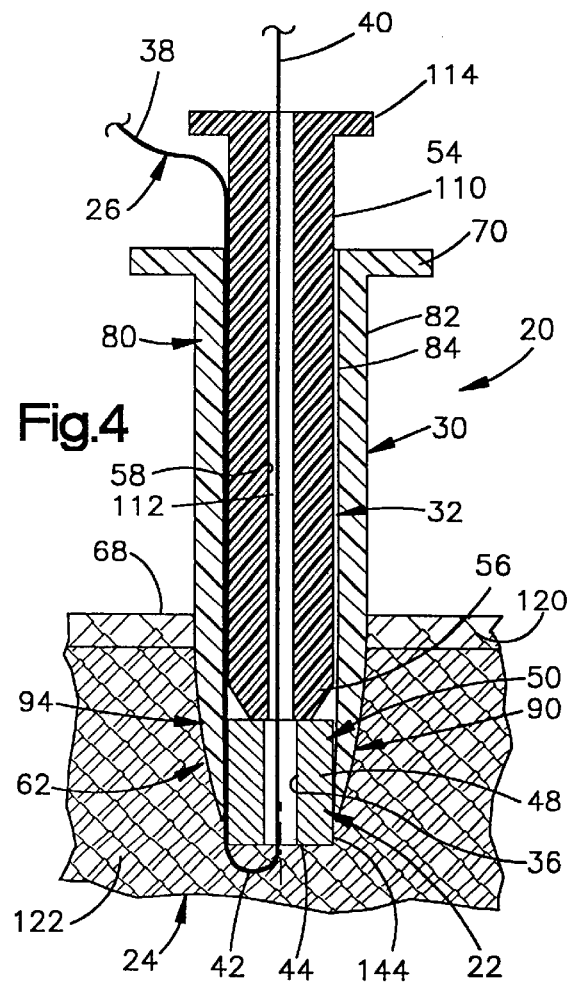
FIG. 4 is a simplified schematic illustration, generally similar to FIG. 1, illustrating the tubular member in an open condition.

In accordance with one of the features of the present invention, a leading end portion 62 of the tubular outer member 30 is operable between a closed condition (FIGS. 1–3) and an open condition (FIG. 4). When the leading end portion 62 of the tubular outer member 30 is in the closed condition of FIGS. 1 and 2, the leading end portion of the tubular outer member at least partially blocks the passage 32 through the tubular outer member. When the leading end portion 62 of the tubular outer member 30 is in the closed condition, the leading end portion 62 of the tubular outer member 30 prevents movement of the suture anchor 22 out of the passage 32 in the tubular outer member. In addition, when the leading end portion 62 of the tubular outer member 30 is in the closed condition, the leading end portion of the tubular outer member prevents movement of foreign material, such as body tissue, into the passage 32.

The leading end portion 62 of the tubular outer member 30 is operable from the closed condition of FIG. 1 to the open condition of FIG. 4. When the leading end portion 62 of the tubular outer member 30 is in the open condition, the suture anchor 22 can be moved out of the passage 32 under the influence of force applied against the trailing end portion 50 of the suture anchor by the tubular inner member 54. As this occurs, the suture anchor 22 moves into the body tissue 24.

To operate the leading end portion 62 of the tubular outer member 30 from the closed condition of FIG. 1 to the open condition of FIG. 4, force is applied against the inside of the passage 32 through the tubular outer member 30. The force applied against the inside of the passage 32 operates the leading end portion 62 of the tubular outer member 30 from the closed or contracted condition of FIG. 1 to the open or expanded condition of FIG. 4. Pressure applied against the leading end portion 62 of the tubular outer member 30 effects expansion of the tubular outer member from the closed condition to the open condition.

In accordance with another feature of the invention, the leading end portion 62 of the tubular outer member 30 is pointed to facilitate piercing of body tissue 24 with the leading end portion of the tubular outer member. When the tubular outer member 30 is in the closed condition of FIG. 1, a point 66 is formed at the end of the tubular outer member 30. This point can initiate the formation of an opening in an imperforate surface 68 on the body tissue 24. In addition, as force is manually applied against a handle 70 connected with the tubular outer member 30, the point 66 continues to pierce body tissue as the tubular member 30 moves into the body tissue.

It is believed that the point 66 on the leading end of the tubular member 30 will be particularly advantageous in piercing soft body tissue. However, it should be understood that the inserter assembly 20 can be utilized with hard body tissue, such as bone. When the inserter assembly 20 is used with hard body tissue, an opening will be drilled or otherwise preformed in the hard body tissue. The leading end portion 62 of the tubular outer member 30 \will be inserted into the preformed opening in the hard body tissue.

Figure 2:
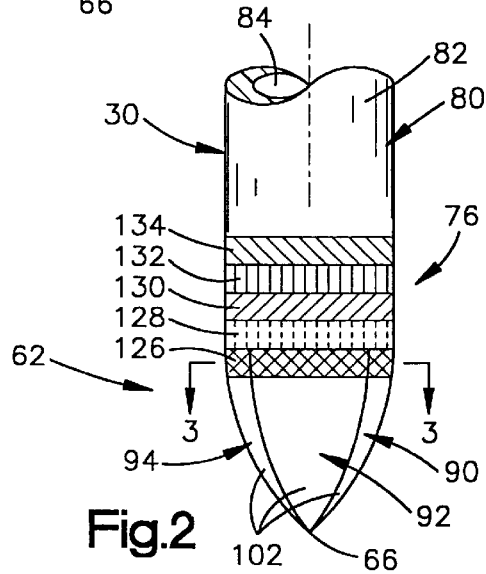
FIG. 2 is a fragmentary pictorial illustration of a portion of the tubular member of FIG. 1 and illustrates indicia on an outer side of the tubular member.

During insertion of the leading end portion 62 of the tubular outer member 30 into the preformed opening in the body tissue, the leading end portion 62 of the tubular member will be in the closed condition illustrated in FIGS. 1 and 2. After the tubular outer member 30 has been inserted into the preformed opening in the hard body tissue, the leading end portion 62 of the tubular outer member will be operated to the open condition of FIG. 4 by force transmitted from the tubular inner member 54.

In accordance with another feature of the present invention, indicia 76 is provided on the outside of the tubular outer member 30. The indicia 76 indicates the distance through which the tubular outer member 76 has been inserted into the body tissue 24. Thus, as the tubular outer member 30 of the inserter assembly 20 is inserted into the body tissue 24, the body tissue covers the indicia. When indicia corresponding to a desired depth of insertion of the tubular outer member 30 in the body tissue 24 has been covered by body tissue, movement of the tubular outer member into the body tissue is interrupted.

Although it is preferred to insert the leading end portion 62 of the tubular outer member 30 into body tissue, the leading end portion of the tubular member may merely be positioned closely adjacent to a preformed opening in the body tissue. Thus, the leading end portion of the tubular outer member 30 may merely be positioned in axial alignment with an opening drilled in bone.

Inserter Assembly—Embodiment of FIGS. 1–4

The tubular outer member 30 (FIG. 1) of the inserter assembly 20 is integrally formed as one piece of polymeric material. The tubular outer member 30 has a rigid cylindrical main or body portion 80. The main or body portion 80 has a cylindrical outer side surface 82 and a cylindrical inner side surface 84 which is coaxial with the outer side surface. The inner side surface 84 at least partially defines the cylindrical passage 32 which extends through the tubular outer member 30.

The cylindrical inner side surface 84 on the main or body portion 80 has a diameter which is slightly greater than an outside diameter of the cylindrical suture anchor 22. This enables the cylindrical suture anchor 22 to move easily along the main or body portion 80 of the tubular outer member 30. The outer leg or portion 38 of the suture 26 extends between the suture anchor 22 and the inner side surface 84 of the main or body portion 80 of the tubular outer member 30.

Although the suture anchor 22 could have many different sizes and configurations, the illustrated suture anchor is cylindrical. The suture anchor 22 has a length of about two millimeters. The suture anchor 22 has an outside diameter of about one millimeter and an inside diameter of about one-half millimeter. The foregoing specific dimension for the suture anchor 22 may vary and have been set forth herein only for purposes of clarity of description.

Figure 3:
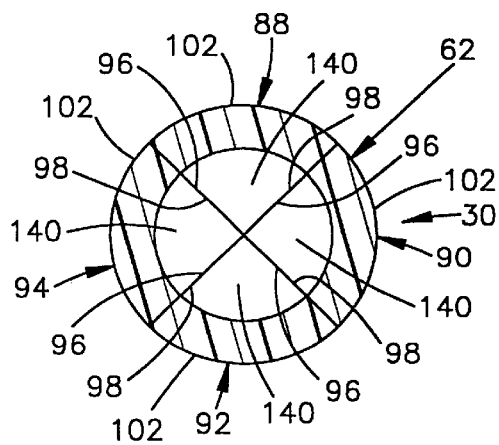
FIG. 3 is a sectional view, taken generally along the line 3—3 of FIG. 2, further illustrating the construction of the tubular member.

The leading end portion 62 of the tubular outer member 30 is formed by a plurality of segments 88, 90, 92, and 94 (FIG. 3). Each of the segments 88, 90, 92 and 94 has a pair of opposite side surfaces 96 and 98 which extend from the point 66 (FIGS. 1 and 2) to the main or body portion 80 of the tubular outer member 30.

When the tubular outer member 30 is in the closed condition of FIGS. 1–3, the segments 88–94 completely block the leading end portion 62 of the tubular outer member 30 and form the point 66. Thus, when the tubular outer member 30 is in the closed condition, the side surfaces 96 and 98 on each of the segments 88–94 are disposed in abutting engagement with the side surfaces on adjacent segments. The segments 88–94 cooperate to provide the pointed leading end portion 60 with a generally conical configuration (FIGS. 1 and 2). If desired, spaces could be provided between the segments 88–94 when the tubular outer member 30 is in the closed condition.

When the tubular outer member 30 pierces body tissue 24 (FIG. 1), the body tissue applies force against an outer side surface 102 (FIGS. 2 and 3) on each of the segments 88–94. Pressure applied against the outer side surfaces 102 of the segments 88–94 presses the side surfaces 96 and 98 on the adjacent segments together. Thus, force applied against the segments 88–94 by the body tissue 24 as the tubular outer member 30 penetrates the body tissue urges the leading end portion 62 of the tubular outer member toward the conical closed condition of FIGS. 1–3.

The closed leading end portion 62 of the tubular outer member 30 is completely blocked by the segments 88–94. Therefore, it is impossible for the body tissue to enter the passage 32 in the tubular outer member 30 as the tubular outer member is inserted into the body tissue. However, if desired, the closed leading end portion 62 of the tubular outer member 30 may be only partially blocked by the segments 88–94. For example, small spaces or slots could be located between the segments 88–94 at locations axially spaced from the point 66. Alternatively, the spaces or slots could extend to the point 66.

The tubular inner member 54 (FIG. 1) is disposed in a coaxial relationship with the tubular outer member 30 and the cylindrical anchor 22. The tubular inner member 54 is integrally formed of one piece of rigid polymeric material. The tubular inner member 54 has a cylindrical outer side surface 110 with a diameter which is smaller than the diameter of the cylindrical inner side surface 84 of the tubular outer member 30. This enables the tubular inner member to move freely along the main or body portion 80 of the tubular outer member 30.

The passage 58 in the tubular inner member 54 has a cylindrical inner side surface 112 which is disposed in a coaxial relationship with the cylindrical outer side surface 110. The inner leg or portion 40 of the suture 26 extends through the cylindrical passage 58 in the inner member 54. A suitable handle 114 is provided on an axially outer end portion of the tubular inner member 54.

When a suture 26 is to be positioned in the body tissue 24 and held in place by the suture anchor 22, the suture is first threaded through the center of the passage 36 in the anchor 22. The inner leg or portion 40 of the suture 26 is then threaded through the passage 58 in the tubular outer member 54. The suture anchor 22 and tubular outer member 54 are then moved into the passage 42 in the tubular outer member 30 (FIG. 1). At this time, the leading end portion 62 of the tubular outer member 30 is in the closed condition and blocks movement of the anchor 22 out of the passage 32 through the leading end portion 62 of the tubular outer member.

When the anchor 22 is to be inserted into the body tissue 24, the point 66 on the leading end portion of the tubular outer member 30 may be moved into engagement with the imperforate outer surface 68 on skin 120 of a patient. Force is then manually applied against the handle 70 on the tubular outer member 30. This force causes the point 66 on the tubular outer member 30 to initiate the formation of an opening in the outer surface of the skin 120.

Continued manual application of force against a handle 70 on the tubular outer member 30 results in the point 68 moving through the skin 120 and piercing the flesh 122 disposed beneath the skin. As the leading end portion 62 of the tubular outer member 30 pierces the flesh 122, the viscoelastic material of the flesh is pressed aside and the tubular outer member 30 penetrates the body tissue 24.

As the tubular outer member 30 moves into the body tissue 24, the indicia 76 (FIG. 2) on the tubular outer member 30 is partially covered by the body tissue. In the illustrated embodiment of the invention, the indicia 76 includes a plurality of stripes 126, 128, 130, 132 and 134 (FIG. 2) of different colors. As the tubular outer member 30 moves into the body tissue, the lowermost (as viewed in FIG. 2) stripe 126 is covered. As the tubular outer member 30 moves further into the body tissue, the remaining stripes are sequentially covered by the body tissue.

When one of the stripes 126–134 corresponding to a desired depth of insertion of the tubular outer member 30 is at least partially covered by body tissue, the surgeon is informed that the desired depth of penetration has been obtained. Movement of the tubular outer member 30 into the body tissue is then interrupted. Thus, the stripes 126–134 measure the depth to which the tubular outer member 30 has been inserted into the body tissue 24.

In the illustrated embodiment of the invention, the measurement of the depth to which the tubular outer member 30 is inserted into the body tissue 24 is provided by the multi-colored strips 126–134. Alternatively, numerical indicia indicative of the distance which the tubular outer member 30 is moved into the body tissue could be provided on the outside of the tubular outer member. Of course, other indicia could be utilized if desired.

When the indicia 76 indicates that the tubular outer member 30 has moved to the desired depth into the body tissue 24 downward (as viewed in FIG. 1) movement of the tubular outer member 30 into the body tissue is interrupted. The leading end portion 62 of the tubular outer member 30 is then operated from the closed condition of FIG. 1 to the open condition of FIG. 4. The suture anchor 22 is moved through the open leading end portion 62 of the tubular outer member 30 into the body tissue 24.

When the leading end portion 62 of the tubular outer member 30 is to be operated from the closed condition of FIG. 1 to the open condition of FIG. 4, the tubular inner member 54 is manually pressed against the annular trailing end portion 50 of the suture anchor 22. This moves the annular leading end portion 44 of the suture anchor 22 into engagement with inner side surfaces 140 on the segments 88–94. Force applied against the inner side surfaces 140 of the segments 88–94 by the suture anchor 22 resiliently cams or forces the segments 88–94 away from each other to expand the end portion 62 of the tubular outer member 30.

Thus, as the suture anchor 22 moves axially downward (as viewed in FIG. 1) in the passage 32 into the closed leading end portion 62 of the tubular outer member 30, the suture anchor applies force against the inner side surface 140 on each of the segments 88–94. This force moves the segments 88–94 apart to expand the passage 32 and the end portion 62 of the tubular outer member 30. Continued axial movement of the suture anchor 22 into the leading end portion 62 of the tubular outer member 30 increases the distance which the outer or lower end portions of the segments 88–94 move apart.

Still further movement of the suture anchor into the leading end portion 62 of the tubular outer member 30 cams the segments 88–94 to the fully open position of FIG. 4. The leading end portion 44 of the suture anchor 22 then moves through a circular space between axially outer tips of the segments 88–94. As this occurs, the natural resilience of the segments 88–94 presses them against a cylindrical outer side surface 144 of the anchor 22. This results in the segments 88–94 of the leading end portion 62 of the tubular outer member 30 being held in the open condition of FIG. 4 by the anchor 22.

Continued downward (as viewed in FIG. 4) movement of the tubular inner member 54 pushes the anchor 22 through the open leading end portion 62 of the tubular outer member 30. As the anchor 22 is pushed through the open leading end portion 62 of the tubular outer member 30, the inner side surfaces 140 of the segments 88–94 slide along and press firmly against the cylindrical outer side surface 144 of the anchor. Thus, the suture anchor 22 is firmly gripped by the end portion 62 of the tubular outer member 30 as the suture anchor moves into the body tissue 24. This enables the tubular outer member 30 to hold the suture anchor 22 in a desired orientation as the suture anchor is moved into the body tissue 24.

When the trailing end portion 50 of the anchor moves out of the open end portion 62 of the tubular outer member 30, the leading end portion 56 of the tubular inner member 54 has moved into the open leading end portion of the tubular outer member. Continued axially downward (as viewed in FIG. 4) movement of the tubular inner member 54 moves the tubular inner member through the open leading end portion 62 of the tubular outer member 30. If desired, the tubular inner member 54 can then be utilized to apply force against the trailing end portion 50 of the anchor 22 as force is applied to the outer leg 38 of the suture 26 to change the orientation of the anchor 22 relative to the body tissue 24 and inserter assembly 20 in the manner disclosed in U.S. Pat. No. 5,522,846 issued Jun. 4, 1996 to Peter M. Bonutti. Of course, if desired, the suture anchor 22 could remain in the orientation shown in FIG. 4.

Once the suture anchor 22 has been moved into the body tissue 24, the inserter assembly 20 is withdrawn from the body tissue. Since the tubular inner member 54 has moved into the open leading end portion 62 of the tubular outer member 30, the leading end portion of the tubular outer member is maintained in the open condition by the presence of the tubular outer member 54. Thus, the inner side surfaces 140 of the segments 88–94 are pressed firmly against the cylindrical outer side surface 110 of the tubular inner member by the natural resilience of the segments. This results in the leading end portion 62 of the tubular outer member 30 being maintained in the open condition as the inserter assembly is withdrawn from the body tissue.

In the embodiment of the invention illustrated in FIGS. 1–4, the suture anchor 22 has a cylindrical configuration. Therefore, the tubular outer member 30 and tubular inner member 54 have cylindrical configurations. However, it is contemplated that the suture anchor 22 could have a polygonal cross-sectional configuration. The tubular outer member 30 and inner member 54 may have a corresponding polygonal cross-sectional configuration.

The foregoing description of the embodiment of the invention illustrated in FIGS. 1–4 has been in conjunction with insertion of the suture anchor 22 into the soft body tissue 24. When the suture anchor 22 is to be inserted into bone, an opening is drilled through a hard outer layer of the bone into soft inner material of the bone. Once this has been done, the tubular outer member 30 is inserted into the opening in the bone. The closed leading end portion 62 of the tubular outer member 30 is then operated from the closed condition of FIG. 4. The anchor 22 is moved through the open end portion 62 of the tubular outer member 30 into the bone.

It is contemplated that the inserter assembly 20 may be used to position an anchor 22 in either soft or hard tissue at many different locations in a patient's body. The point 66 on the end portion 62 of the outer tubular member 30 may be used to pierce body tissue at locations remote from a patient's skin 120. Thus, the inserter assembly 20 may be used to position a suture anchor 22 in an organ within the patient's body.

When the inserter assembly 20 is to be used to position the suture anchor 22 in hard body tissue, such as the hard outer or cortical layer of bone, the point 66 may be omitted from the leading end portion 62 of the tubular outer member 30. When the inserter assembly 20 is to be used to position the anchor 22 in the soft body tissue 24, the formation of an opening in the body tissue may be initiated without piercing imperforate body tissue with the point 66. Thus, an opening could be formed in the patient's skin 120 and/or flesh 122 with a suitable cutting instrument. However, it is believed that it may be preferred to use the point 66 to form an opening in the skin 120 and/or flesh 122.

Inserter Assembly—Embodiment of FIGS. 5–8

In the embodiment of the invention illustrated in FIGS. 1–4, the tubular outer member 30 is formed of a single piece of polymeric material. In the embodiment of the invention illustrated in FIGS. 5–8, the tubular outer member is formed by a sheath which encloses a plurality of wires. Since the embodiment of the invention illustrated in FIGS. 5–8 is generally similar to the embodiment of the invention illustrated in FIGS. 1–4, similar numerals will be utilized to designate similar components, the suffix letter "a" being associated with the numerals of FIGS. 5–8 to avoid confusion.

Figures 8, 9:
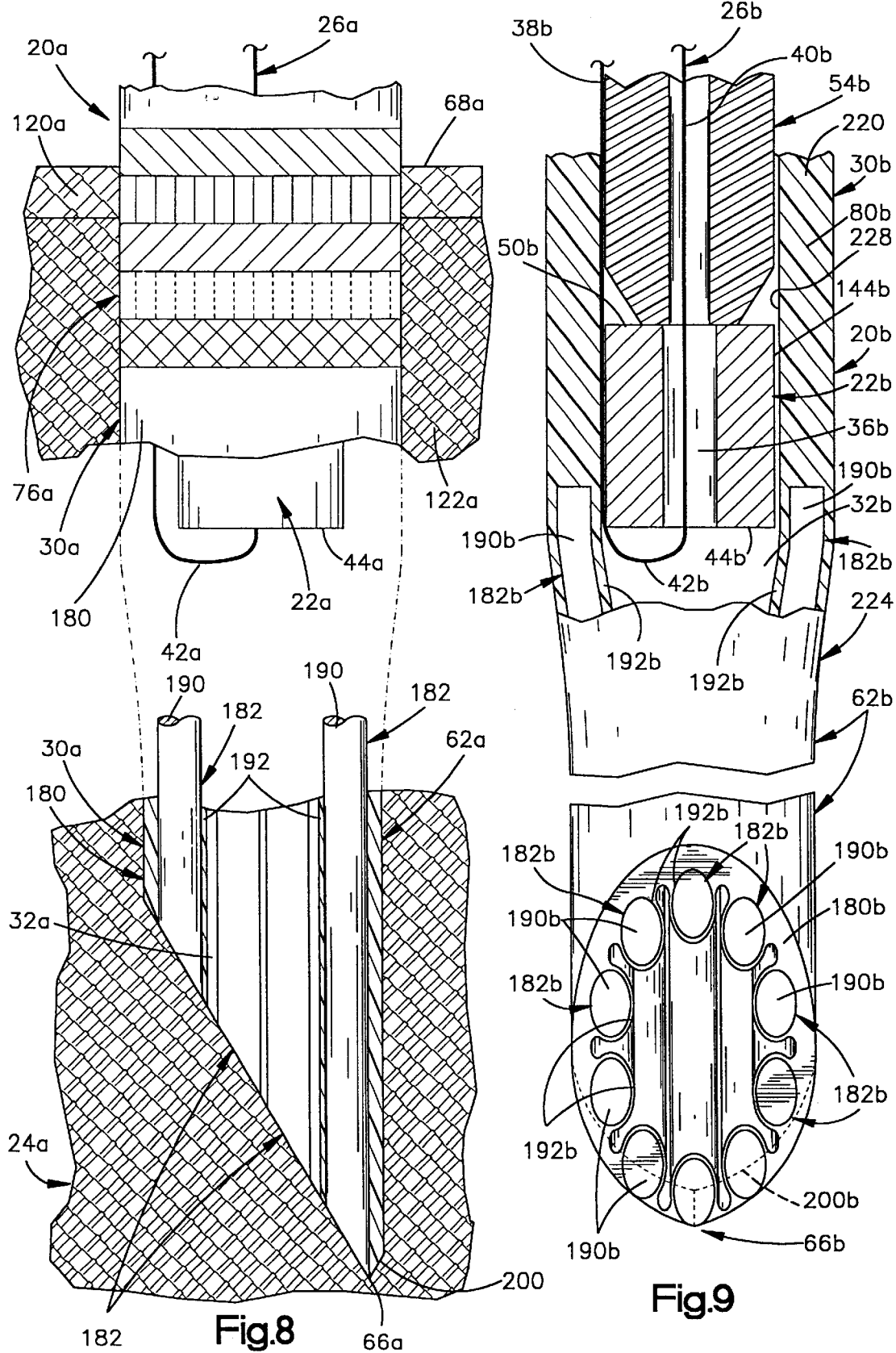
FIG. 8 is an enlarged simplified schematic illustration of the manner in which the inserter assembly of FIGS. 5–7 is inserted into body tissue.
FIG. 9 is an enlarged simplified schematic sectional view, generally similar to FIGS. 6 and 8, of a third embodiment of the inserter assembly.

An inserter assembly 20a is utilized to position a suture anchor 22a (FIGS. 6–8) in body tissue 24a (FIG. 8). A suture 26a extends through the suture anchor 22a. The suture anchor 22a has a cylindrical configuration. However, the suture anchor 22a could have a polygonal configuration if desired. The suture anchor 22a has a length of about two millimeters and an outside diameter of about one millimeter. However, it is contemplated that the suture anchor 22a will have many different sizes and configurations. The invention is not to be limited to the foregoing specific sizes and configurations for the suture anchor 22a.

The inserter assembly 20a (FIG. 5) includes a cylindrical tubular outer member 30a having a cylindrical passage 32a through which the suture anchor 22a moves into body tissue 24a (FIG. 8) with the suture 26a extending through the suture anchor. The suture 26a includes inner and outer legs or portions 38a and 40a (FIGS. 5 and 6) which are interconnected by a connector portion 42a (FIG. 6). The inner leg 40a of the suture 26a extends through a cylindrical passage 36a in the anchor 22a. The connector portion 42a of the suture 26a extends across an annular leading end portion 44a of the suture anchor 22a. The outer leg or portion 48a of the suture 26a extends along a cylindrical outer side surface 144a of the suture anchor 22a.

A cylindrical tubular inner member 54a (FIGS. 5 and 6) engages an annular trailing end portion 50a (FIG. 6) of the cylindrical suture anchor 22a. The tubular inner member 54a extends into the tubular outer member 30a. The tubular inner member 54a is disposed in a coaxial relationship with the cylindrical tubular outer member 30a.

Prior to insertion of the anchor 22a and tubular outer member 30a, the tubular outer member is resiliently contracted to a closed condition. When the tubular outer member 30a is in the closed condition, a passage 32a through the tubular outer member is only partially blocked. When the tubular outer member 30a is in the closed condition, the passage 32a has a relatively small cross-sectional area. This cross-sectional area is small enough to prevent movement of foreign material, such as body tissue, into the passage 32a.

As the suture anchor 22a is moved axially through the tubular outer member 30a (FIG. 6) under the influence of force applied against the suture anchor by the inner member 54a, the suture anchor expands the tubular outer member from the closed condition to an open condition. Thus, force applied against the inside of the passage 32a results in resilient expansion of the passage from the closed condition to the open condition.

The tubular outer member 30a has a pointed leading end portion 62a (FIG. 5) to pierce body tissue when the leading end portion of the tubular outer member 30a is in the closed condition. The leading end portion 62a of the tubular outer member 30a has a point 66a which pierces an imperforate surface 68a (FIG. 8) on the body tissue 24a during insertion of the tubular outer member 30a into the body tissue. Although it is preferred to have the pointed leading end portion 62a initiate the formation of an opening 68a in the imperforate surface 68a of the soft body tissue 24a, it is contemplated that an incision or other opening could be preformed in the body tissue 24a if desired.

Although the pointed leading end portion 62a of the tubular outer member 30a is particularly well adapted to insertion of the anchor 22a into soft body tissue 24a, it is contemplated that the inserter assembly 20a could be utilized to position an anchor 22a in hard body tissue, such as bone. When the inserter assembly 20a is used to position the anchor 22a in hard body tissue, such as bone, it is contemplated that a preformed opening will be formed in the hard body tissue to receive the suture anchor 22a. For example, an opening could be drilled or otherwise formed through the hard outer layer of bone into the soft inner layer of bone in a manner similar to that disclosed in the aforementioned U.S. Pat. No. 5,522,846.

Indicia 76a (FIG. 8) is provided on the outside of the tubular outer member 30a to indicate the depth of insertion of the tubular outer member into the body tissue 24a. Thus, as the tubular outer member 30a is inserted into the body tissue 24a, the indicia 76a is gradually covered by the body tissue. When the indicia indicates that the tubular outer member 30a has been inserted into the body tissue 24a to a desired depth, movement of the tubular outer member 30a into the body tissue is interrupted and the anchor 22a is inserted into the body tissue.

In accordance with a feature of this embodiment of the invention, the tubular outer member 30a includes an elastic sheath 180 (FIGS. 5–8) which encloses a plurality of longitudinally extending wires 182. The wires 182 and sheath 180 define the passage 32a along which the anchor 22a is moved into the body tissue. At a proximal portion of the inserter assembly 20a, the wires 182 and sheath 180 are clamped between a pair of annular ring members 186 and 188 (FIG. 5).

In the illustrated embodiment of the invention, each of the wires 182 (FIG. 7) includes a central core 190 and a coating or jacket 192. The jacket 192 is integrally formed as one piece with the sheath 180. The cores 190 and jackets 192 of the wires 182 extend between opposite ends of the sheath 180 and are enclosed by the sheath.

The jacket 192 around the core 190 of each of the wires 182 is integrally formed as one piece with the sheath 180. Thus, each of the jackets 192 is formed of the same elastic material as the sheath 180. The elastic polymeric material of the sheath 180 and the jackets 192 may be molded or extruded around the cores 190 during formation of the sheath.

The core 190 and jacket 192 of each of the wires 182 extends parallel to a longitudinal central axis 196 (FIG. 6) of the tubular outer member 30a. The cores 190 and jackets 192 extend throughout the entire length of the sheath 180. Since the jackets 192 are integrally formed as one piece with the sheath 180, the wires 182 are maintained in a parallel relationship with the longitudinal central axis 196 of the tubular outer member 30a. The parallel wires 182 extend from the outer end of the leading end portion 62a (FIGS. 5 and 8) of the tubular outer member 30a to the location where the proximal end of the sheath 180 is clamped between the ring members 186 and 188 (FIG. 5). The wires 182 do not intersect.

The cores 190 of the wires may be formed of any desired material. In the embodiment of the invention illustrated in FIGS. 5–8, the cores 190 are formed of metal. Thus, the cores 190 are formed of music wire, that is a thin gauge steel of about 0.015 inches in diameter. However, the cores 190 could be formed of composite polymeric materials if desired. For example, the cores 190 could be formed by a matrix of polymeric materials strengthened by longitudinally extending carbon fibers.

It should be understood that the use of the term "wire" and/or "core" in this application and its claims does not limit the invention to metal wires. The "wires" may be made of any desired material. For example, the wires 182 may be formed of the same material as the sheath 180. If the wires 182 are formed separately from the sheath 180, a suitable adhesive, such as rubber cement or cyanoacrylate or a similar adhesive may be used to bond the sheath 180 with the wires.

The sheath 180 may be formed of latex or silicone, or of "C-Flex" (trademark), a general purpose thermoplastic elastomer sold by Linvatec Corporation of Clearwater, Florida. It should be understood that the wires 182 could be integrally formed as one piece with the sheath 180 and of the same material as the sheath. Thus, the wires 182 and sheath 180 cold be extruded as one piece of resilient polymeric material. It is also contemplated that the wires 182 could be formed separately from the sheath and loosely positioned in engagement with an inner side surface of the sheath. If the wires 182 are formed separately from the sheath 180, the rings 186 and 188 would clamp the ends of the wires and the sheath together to hold the wires against axial movement relative to the sheath. It should be understood that the jackets 192 could be eliminated from the wires 182 if desired.

In the illustrated embodiment of the invention, the parallel cores 190 of the wires 182 have a cylindrical configuration. Thus, each of the cores 190 has a circular cross-sectional configuration (FIG. 7) in a plane extending perpendicular to the longitudinal central axis of the core. In the embodiment of the invention illustrated in FIGS. 5–8, the sheath engages longitudinally extending side portions of the cores 190.

The surface portions of the cores 190 which do not engage the sheath 180 are enclosed by the jackets 192. Since the jackets 192 are integrally formed as one piece with the sheath 180, there is no precise line of demarcation between the jackets and the sheath. However, the jackets 192 extend inward from the sheath 180 toward the central axis 196 of the tubular outer member 30a and cooperate with the sheath to enclose each of the cores 190. If desired, the jackets 192 could extend completely around the cores 190.

Circular axial end faces of the cores 190 are exposed at opposite ends of the sheath 180. Thus, at the leading end portion 62a (FIG. 8) of the tubular outer member 30a, the circular end faces of the cores 190 are visible. The jackets 192 extend from the end faces of the cores to the opposite end of the sheath. If desired, the jackets 192 could extend across the end faces of the cores 190.

The tubular outer member 30a of the inserter assembly 20a may have the same construction as is disclosed in U.S. Pat. No. 5,320,611 issued Jun. 14, 1994 to Bonutti et al. The specific embodiment of the tubular outer member 30a illustrated in FIGS. 5–8 has a sheath 180 which is integrally formed with jackets 192 around cores 190 of wires 182 in the same manner as is disclosed in U.S. Pat. No. 08/470,142 filed Jun. 6, 1995 by Peter M. Bonutti, et al. and entitled "Method of Using Expandable Cannula".

The natural resilience of the sheath 180 contracts the tubular outer member 30a to the closed condition. When the tubular outer member 30a is in the closed condition, there is a very small opening at the leading end portion 62a of the tubular outer member 30a. This opening is small enough so that any foreign materials, such as body tissue, which may enter the opening are insufficient to cause problems which may effect operation of the inserter assembly 20a.

The leading end portion 62a of the tubular outer member 30a has a point 66a (FIGS. 5 and 8) which facilitates the piercing of body tissue with the tubular outer member. The point at the leading end portion 62a of the tubular outer member 32a is formed by cutting the material of the sheath 180 and wires 182 at an angle of approximately 30° to the longitudinal central axis 196 of the tubular outer member 30a (FIG. 8). Of course, the pointed leading end portion 62a of the tubular outer member 30a could be skewed at a different angle relative to the longitudinal central axis of the tubular outer member if desired.

The ends of the wires 182 and the end of the sheath 180 cooperate to provide the tubular outer member 30a with a leading end portion 62a which can cut body tissue when the leading end portion 62a of the tubular outer member 30a is pressed against the body tissue. The sheath may advantageously be cut away adjacent to the apex of the point 66a. Thus, a beveled surface 200 is formed in the material of the sheath 180 adjacent to the apex of the point 66a. The beveled surface 200 makes the pointed leading end portion 62a of the tubular outer member 30a sharper to facilitate the severing of body tissue.

In the illustrated embodiment of the invention, the cylindrical cores 190 of the parallel wires 182 are formed by thin gauge steel wire. The leading end portion of one of the cores 190 extends through the apex of the point 66a at the leading end portion 62a of the tubular outer member 30a. The leading end of the core 190 of the wire 182 through the apex of the point 66a provides a relatively sharp cutting edge at the axially outer end of the tubular outer member 30a. This sharp cutting edge can readily penetrate relatively tough body tissue.

When the pointed leading end portion 62a of the tubular outer member 30a is pressed against the imperforate outer surface 68a (FIG. 8) on the body tissue 24a with the tubular outer member 30a in the closed or contracted condition, force is transmitted axially through the wires 182 and through the sheath 180 to the body tissue 24a. The apex of the point 66a penetrates the body tissue and initiates the formation of an opening in the imperforate surface 68a of the body tissue 24a.

The initiating of the opening in the imperforate surface 68a of the body tissue 24a is facilitated by having the exposed relatively sharp end of the core 190 and the wire 182 which extends through the apex of the point 66a engage the body tissue to initially cut the imperforate surface of the body tissue. The leading edges of portions or segments of the sheath 180 disposed adjacent to opposite sides of the core 190 of the wire 182 which extends through the apex of the point 66a then severs the body tissue to increase the size of the opening. Thus, the sheath 180 and the ends of the wires 182 cooperate to form an opening in the body tissue 24a The size of the initial opening formed in the body tissue by the point 66a on the leading end portion 62a of the tubular outer member 30a is relatively small. The size of the opening increases until the entire leading end portion 62a of the tubular outer member can be inserted into the opening. It should be understood that, at this time, the leading end portion 62a of the tubular outer member 30a is contracted and has a relatively small outside diameter.

Once the tubular outer member 30a has been inserted into the body tissue 24a to a desired depth, as indicated by the indicia 76a (FIG. 8), the tubular outer member is operated from the closed condition to the open condition. To operate the tubular outer member 30a from the closed condition to the open condition, the suture anchor 22a is pushed axially along the tubular outer member by the tubular inner member 54a (FIG. 6). As the suture anchor 22a is pushed along the tubular outer member 30a, the tubular outer member is expanded from the contracted or closed condition to the open condition. As this occurs, the viscoelastic material of a body tissue is resiliently stretched and the size of the small opening formed by the contracted outer member 30a is increased.

To expand the tubular outer member 30a and move the suture anchor 22a into the body tissue 24a, the cylindrical anchor 22a is moved axially along the passage 32a in the tubular outer member. As the suture anchor 22a is moved downward, as viewed in FIG. 6, along the passage 32a, the cylindrical outer side surface 144a of the suture anchor 22a engages the jackets 192 on the wires 182 (FIG. 7). Force is transmitted from the outer side surface 144a of the suture anchor 22a to the wires 182. This force is transmitted from the wires 182 to the sheath 180. Linear segments of the sheath 180 disposed between the wires 182 are resiliently stretched as the tubular outer member 30*a* is expanded by movement of the suture anchor 22*a* along the passage 32*a*.

The wires 182 hold the outer side surface 144*a* on the suture anchor 22*a* in a spaced apart relationship with the sheath 180. Therefore, there is substantially line contact between the straight longitudinally extending wires 182 and the outer side surface 144*a* of the suture anchor 22*a*. The relatively small linear areas of line contact between the wires 182 and the outer side surface 144*a* of the suture anchor 22*a* (FIG. 7) facilitates axial movement of the suture anchor 22*a* along the passage 32*a*. At this time, the outer leg or portion 38*a* of the suture 26*a* is disposed between a pair of adjacent wires 182 (FIGS. 6 and 7).

The inner member 54*a* has a cylindrical outer side surface 110*a* (FIG. 6) with the same diameter as the outer side surface 144*a* of the anchor 22*a*. Therefore, once a portion of the tubular outer member 30*a* has been resiliently expanded from the closed condition to the open condition, the tubular inner member 54*a* holds the tubular outer member 30*a* in the expanded condition. The wires 182 hold the cylindrical outer side surface 110*a* on the tubular member inner member 54*a* in a spaced apart relationship with the sheath 180. There is substantially line contact between the straight wires 182 and the cylindrical outer side surface 110*a* of the inner member 54*a*.

As the tubular inner member 54*a* continues to move into the tubular outer member 30*a*, the suture anchor 22*a* is pushed through the open leading end portion 62*a* of the tubular outer member 30*a* into the body tissue 24*a*. As the leading end portion 44*a* of the suture anchor 22*a* moves out of the tubular outer member 30*a*, resiliently deflected segments of the sheath 180 disposed between the wires 182 press the wires against the suture anchor. Thus, the suture anchor 22*a* is firmly gripped by the wires 182 as the suture anchor moves into the body tissue. If desired, the orientation of the anchor 22*a* relative to the tubular outer member 30*a* and body tissue 24*a* can be changed by pivoting the suture anchor in the body tissue in the manner disclosed in the aforementioned U.S. Pat. No. 5,522,846.

Inserter Assembly—Embodiment of FIG. 9

In the embodiment of the invention illustrated in FIGS. 5–8, the wires 180 extend axially between opposite ends of the tubular outer member 30*a*. In the embodiment of the invention illustrated in FIG. 9, the wires extend through only a portion of the tubular outer member. Since the embodiment of the invention illustrated in FIG. 9 is generally similar to the embodiment of the invention illustrated in FIGS. 5–8, similar numerals will be utilized to designate similar components, the suffix "b" being associated with the numerals of FIG. 9 to avoid confusion.

An inserter assembly 20*b* is utilized to position a suture anchor 22*b* in body tissue. A suture 26*b* has an outer leg or portion 38*b* which extends along a cylindrical outer side surface 144*b* of the suture anchor 22*b* and an inner leg or portion 40*b* which extends through a cylindrical passage 36*b* in the suture anchor 22*b*. A connector portion 42*b* interconnects the two leg portions 38*b* and 40*b* of the suture 26*b*.

A tubular outer member 30*b* has a central passage 32*b*. The passage 32*b* extends through a main or body portion 80*b* of the tubular outer member 30*b* and through a leading end portion 62*b* of the tubular outer member 30*b*. A tubular inner member 54*b* is disposed in a coaxial relationship with and is telescopically movable relative to the tubular outer member 30*b*.

The main or body portion 80*b* of the tubular outer member 30*b* is, throughout, most of its length, formed by a sheath or cylindrical wall 220 of polymeric material. Thus, throughout most of its length, the main portion 80*b* of the tubular outer member is formed by a solid cylindrical wall 220 of resilient polymeric material.

The leading end portion 62*b* of the tubular outer member 30*b* has the same construction as the tubular outer member 30*a* of FIGS. 5–8. Thus, the leading end portion 62*b* (FIG. 9) of the tubular outer member 30*b* includes a sheath 180*b* formed of an elastic polymeric material. A plurality of wires 182*b* are enclosed by the sheath 180*b*.

Each of the wires 182*b* includes a core 190*b* which is enclosed by a coating or jacket 192*b*. The cores 190*b* are formed of metal. The jackets 192*b* are integrally formed as one piece with the sheath 180*b*. If desired, the wires 182*b* could be formed of the same material as the sheath 180*b*.

The cores 190*b* and jackets 192*b* extend from the lower (as viewed in FIG. 9) end portion of the cylindrical main or body portion 80*b* of the tubular outer member 30*b* throughout the length of the leading end portion 62*b*. The main or body portion 80*b* of the tubular outer member 30*b* has a relatively large diameter, compared to the diameter of the leading end portion 62*b* of the tubular outer member 30*b*. The cores 190*b* of the wires 182*b* terminate just past a transition portion 224 of the tubular outer member 30*b*. The transition portion 224 of the tubular outer member 30*b* tapers axially downward (as viewed in FIG. 9) and radially inward from the relatively large diameter main or body section 80*b* to the relatively small diameter leading end portion 62*b*.

The wires 182*b* and sheath 180*b* are constructed in the same manner as previously described in conjunction with the embodiment of the invention illustrated in FIGS. 5–8. However, the wires 180*b* of the embodiment of the invention illustrated in FIG. 9 do not extend throughout the entire length of the tubular outer member 30*b*.

The sidewall 220 of the main or body portion 80*b* of the tubular outer member 30*b* is integrally formed as one piece with the sheath 180*b*. However, the sidewall 220 of the main portion 80*b* of the tubular outer member 30*b* has a continuous cylindrical inner side surface 228 with an inside diameter which is just slightly greater than the outside diameter of the suture anchor 22*b* and the tubular outer member 54*b*. Therefore, the suture anchor 22*b* and tubular outer member 54*b* can be freely moved along the main or body portion 80*b* of the tubular outer member 30*b*.

The inside diameter of the transition portion 124 of the tubular outer member 30*b* tapers axially downward (as viewed in FIG. 9) from the relatively large diameter body or main body 80*b* of the tubular outer member to the relatively small diameter leading end portion 62*b* of the tubular outer member. This tapering configuration enables the leading end portion 62*b* of the tubular outer member 30*b* to be in a closed condition partially blocking the passage 32*b* through the tubular outer member 30*b* while the portion of the passage 32*b* disposed in the inner or main portion 80*b* of the tubular outer member is unrestricted. Therefore, the suture anchor 22*b* can freely move through the main portion 80*b* of the tubular outer member 30*b* while passage of the suture anchor 22*b* through the leading end portion 62*b* is blocked.

When the suture anchor 22*b* is to be positioned in body tissue, the pointed leading end portion 62*b* of the tubular outer member may be utilized to initiate the formation of an opening in the body tissue. As the leading end portion 62*b* of the tubular outer member 30*b* moves into the opening, the pointed leading end portion of the tubular outer member continues to pierce the body tissue. If desired, indicia, corresponding to the indicia 76 of FIG. 2, may be provided on the tubular outer member 32b to indicate the depth to which the tubular outer member has penetrated the body tissue.

Once the tubular outer member 30b has penetrated the body tissue to a desired depth, the tubular inner member 54b is pressed against the trailing end portion 50b of the suture anchor 22b. This causes the annular leading end portion 44b of the suture anchor 22b to press against the wires 182b in the transition portion 224 of the tubular outer member 30b. As the suture anchor 22b is moved through the transition portion 224 of the tubular outer member 30b, the outer side surface 144b of the suture anchor 22b slides along the wires 182b and is held in a spaced apart relationship with the sheath 180b. Force is transmitted from the wires 182b to the sheath 180b to resiliently expand the sheath 180b in the transition portion 224 of the tubular outer member.

Continued movement of the tubular inner member 54b into the tubular outer member 30b pushes the suture anchor 22b into the closed leading end portion 62b of the tubular outer member. As this occurs, the outer side surface 144b on the anchor 22b slides along the wires 182b and expands the portion of the sheath 180b in the leading end portion 62b of the tubular outer member 30b. As the anchor 22b approaches the point 66b on the leading end portion 62b of the tubular outer member 30b, the leading end portion 62b of the tubular outer member is operated from the closed condition to an open condition. Thus, the leading end portion 62b of the tubular outer member 30b is expanded by force transmitted from the outer side surface 144b of the anchor 22b through the wires 182b to the sheath 180b. This results in a resilient stretching of the sheath 180b and increasing of the size at the opening of the lower (as viewed in FIG. 9) end of the leading end portion 62b of the tubular outer member 30b.

Once the anchor 22b has been pushed through the opening at the end of the leading end portion 62b of the tubular outer member 32b, the tubular inner member 54b retains the leading end portion 62b of the tubular outer member 30b in the open condition. As the anchor 22b is moved along the transition portion 224 and the leading end portion 62b of the tubular outer member 30b, the outer leg or portion 38b of the suture 26b moves along a space between adjacent wires 182b.

Figure 10:
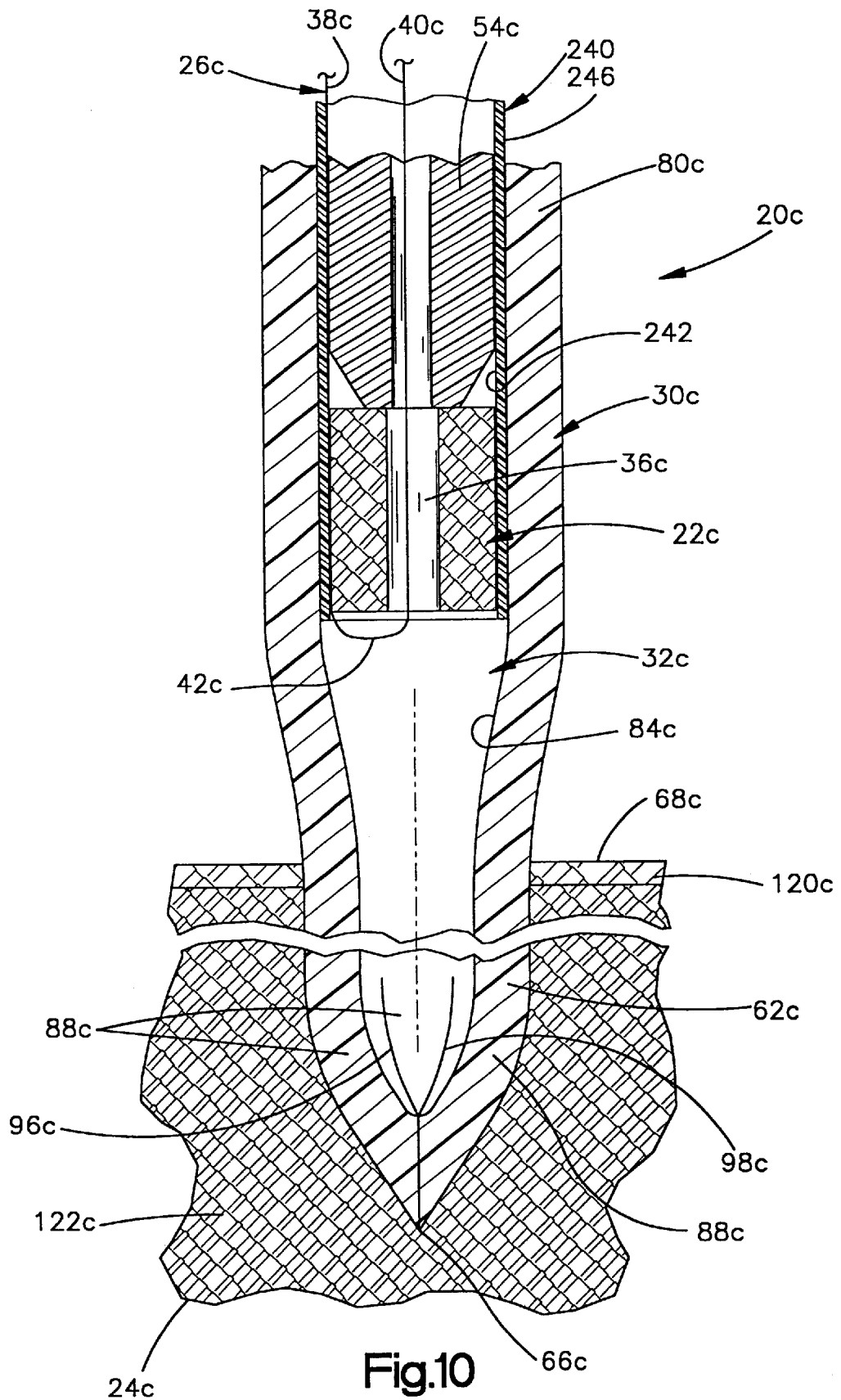
FIG. 10 is an enlarged simplified schematic illustration of the manner in which a fourth embodiment of the inserter assembly is inserted into body tissue.

Inserter Assembly—Embodiment of FIG. 10

In the embodiment of the invention illustrated in FIGS. 5–9, wires are provided in at least a portion of the tubular outer member of the inserter assembly. In the embodiment of the invention illustrated in FIG. 10, the wires are omitted and the tubular outer member has a sidewall which is resiliently deflected to effect operation of the tubular outer member from a closed condition to an open condition. Since the embodiment of the invention illustrated in FIG. 10 is generally similar to the embodiment of the invention illustrated in FIGS. 1–9, similar numerals will be utilized to designate certain components, the suffix "c" being associated with the numerals of FIG. 10 to avoid confusion.

An inserter assembly 20c includes a tubular outer member 30c along which a suture anchor 22c is moved. The tubular outer member 30c includes a main or body portion 80c which is integrally formed as one piece with a leading end portion 62c of the tubular outer member 30c. A passage 32c extends through the main or body portion 80c into the leading end portion 62c. Prior to expansion of the tubular outer member 30c, the passage 32c has the same, relatively small, diameter throughout its length.

The leading end portion 62c of the tubular outer member 30c includes a plurality of segments 88c having the same general construction as the segments 88–94 of the embodiment of the invention illustrated in FIGS. 1–4. The natural resilience of the segments 88c results in side surfaces 96c and 98c on the segments being pressed together to close the pointed end portion 62c of the tubular outer member 30c.

The tubular outer member 30c. is formed of a relatively resilient polymeric material. Therefore, it is preferred to form an incision in an imperforate outer side surface 68c of a patient's skin 120c and then to move a pointed end 66c of the tubular outer member 30c into flesh 122c disposed in the body tissue 24c beneath the skin 68c. As the pointed end portion 66c moves into the flesh 122c, the pointed end portion 66c of the tubular outer member 30c is effective to pierce the body tissue 24c.

Once the tubular outer member 80c has been inserted to a desired depth in the body tissue 24c, the anchor 22c is moved into the body tissue. In the embodiment of the invention illustrated in FIG. 10, the tubular outer member 30c is formed of a resilient polymeric material which has a relatively small diameter, throughout its entire length, prior to movement of the anchor 22c into the tubular outer member. To effect expansion of the tubular outer member 30c and operation of the tubular outer member from the closed condition illustrated in FIG. 10 to an open condition, a rigid tubular cylindrical expansion member 240 is inserted axially into the resiliently expandable tubular outer member 30c.

The tubular expansion member 240 encloses the anchor 22c and at least a portion of the tubular outer or pusher member 54c. A suture 26c has an outer leg or portion 38c which extends between an outer side surface of the anchor 22c and an inner side surface 242 of the expansion member 240. The suture 26c also includes an inner leg 40c which extends through a passage 36c in the suture anchor 22c and through a passage in the tubular inner member 54c. A connector portion 42c of the suture 26c interconnects the two leg portions 38c and 40c.

As the tubular expansion member 240 is moved into the tubular outer member 30c, the anchor 22c and pusher member 54c are moved with the expansion member. A cylindrical outer side surface 246 on the expansion member 240 slides along an inner side surface 84c of the tubular outer member 30c. As this occurs, the outer side surface 240 of the expansion member applies force against the inner side surface 84c of the resilient polymeric material forming the tubular outer member 30c. This results in resilient expansion of the tubular outer member 30c as the expansion member 240 is moved axially into the tubular outer member. As the tubular expansion member 240 moves into the leading end portion 62c of the tubular outer member 30c, the expansion member applies force against inner sides surfaces of the segments 88c of the tubular outer member 30c. This force moves the segments 88c apart and operates the tubular outer member 30c from the closed condition of FIG. 10 to an open condition.

When the segments 88c are in the closed condition of FIG. 10, a passage 32c through the tubular outer member 30c is blocked. As the expansion member 240 moves into the leading end portion 62c of the tubular outer member 30c, the outer side surface 246 of the expansion member applies force against the inner side surfaces of the segments 88c and cams the segments apart. At the same time, the resilient polymeric material of the tubular outer member 30c is expanded to increase the size of the passage 32c to the same size as the expansion member 240. The expansion member 240 is moved into the tubular outer member 30c until it reaches the outermost or lower (as viewed in FIG. 10) ends of the segments 88c. At this time, the tubular inner member 54c can push the anchor 22c through the open outer member 30c into the body tissue 24c.

If desired, indicia corresponding to the indicia 76 of FIG. 2 may be provided on the outside of the tubular outer member 30c. By providing indicia on the outside of the tubular outer member 30c, the depth of penetration of the tubular outer member into the body tissue 24c would be indicated to an observer. Of course, numerical indicia rather than the colored bands of FIG. 2 could be utilized if desired.

Since the suture anchor 22c is enclosed by the rigid expansion member 240, very little force is applied against the suture anchor. In the embodiments of the invention illustrated in FIGS. 5–9, the wires 182 and 182b apply force against the outer side of the suture anchor as the suture anchor is moved through the tubular outer member in the body tissue. In the embodiment of the invention illustrated in FIG. 10, the anchor 22c is enclosed by the tubular expansion member throughout the extent of movement of the anchor through the tubular outer member 30c.

Resilient expansion of the tubular outer member 30c is effected by transmitting force from the expansion member 240 to the resilient material of the tubular outer member 30c. This is accomplished without applying force against the cylindrical outer side surface of the suture anchor 22c. Since relatively little force is applied against the outer side surface of the suture anchor 22c as it is moved into the body tissue 24c, it is contemplated that the suture anchor may be formed of body tissue or other materials. Of course, the expansion member 240 could be utilized in conjunction with a metal suture anchor having the same construction as the suture anchor 22 of FIG. 1.

If the suture anchor 22c (FIG. 10) is formed with a polygonal cross-sectional configuration, it is contemplated that the expansion member 240 would be probably be formed with the same polygonal cross-sectional configuration. This would enable the expansion member 240 to engage flat end surfaces on the suture anchor to position the anchor as it moves with the expansion member along the tubular outer member 30c. If desired, the suture anchor 22c could be formed with the same polygonal configuration as the anchor discloses in the aforementioned U.S. Pat. No. 5,549,630.

Conclusion

An apparatus (FIGS. 1–10) which may be used to position a suture anchor 22 relative to body tissue 24 includes a tubular member 30. The tubular member 30 is advantageously operable between a closed condition at least partially blocking a passage 32 in the tubular member and an open condition in which the tubular member is ineffective to block the passage. By blocking the passage 32 in the tubular member 30, entry of body tissue 24 and/or other foreign matter into the passage in the suture anchor is prevented. In some embodiments of the invention, when the tubular member 30 is in the closed condition, the leading end portion 62 of the tubular member is contracted so as to be readily inserted into body tissue. A point 66 at the contracted end of the tubular member 30 facilitates piercing of body tissue.

Upon movement of a suture anchor 22 through the end portion 62 of the tubular member 30, a leading end portion 44 of the anchor may apply force against the tubular member to effect operation of the tubular member from the closed condition to the open condition. Alternatively, a second member 240 (FIG. 10) may be inserted into the tubular member 30 along with the suture anchor 22. The second member 240 forces against an inner side surface 84 of the tubular member 30 to effect operation of the tubular member from the closed condition to the open condition.

In one specific embodiment of the invention (FIGS. 5–9), the tubular member 30a includes a sheath 180 which encloses a plurality of wires 182. A leading end portion 62a of the sheath 180 may be expanded by applying force against the wires 182 with the anchor. A portion of the suture 26a may be disposed between the wires 182.

Indicia 76 may be provided on the outside of the tubular member 30 to indicate the depth to which the tubular member has been inserted into body tissue 24. When indicia 76 corresponding to a desired depth of insertion of the tubular member 30 in the body tissue 24 has been covered by the body tissue, the step of inserting the tubular member into body tissue is interrupted.

Having described the invention, the following is claimed:

1. A method of positioning an anchor member relative to body tissue, said method comprising the steps of providing a tubular member, said step of providing a tubular member includes providing a tubular member having a plurality of wires which extend along a passage in the tubular member, inserting the tubular member into body tissue by piercing the body tissue with an end portion of the tubular member and moving at least a portion of the tubular member through an opening formed in the body tissue by piercing the body tissue with the end portion of the tubular member, moving the anchor member along a passage in the tubular member, said step of moving the anchor member along the passage in the tubular member includes sliding the anchor member along the wires, and moving the anchor member out of the passage in the tubular member into the body tissue.

2. A method as set forth in claim 1 further including the step of expanding at least a portion of the passage in the tubular member by transmitting force from a leading end portion of the anchor member to the tubular member while moving the anchor member along the passage in the tubular member.

3. A method as set forth in claim 1 wherein said step of piercing the body tissue includes forming an opening in the body tissue at a location which is free of naturally occurring openings.

4. A method as set forth in claim 1 further including the step of expanding at least a portion of the passage in the tubular member by resiliently stretching material which forms at least a portion of the tubular member.

5. A method as set forth in claim 1 further including the step of moving segments of the end portion of tubular member which pierced the body tissue from an initial position in which portions of the segments of the end portion of the tubular member are disposed in engagement with each other to an extended position in which the portions of the segments of the end portion of the tubular member are spaced apart from each other.

6. A method as set forth in claim 1 further including the step of expanding at least a portion of the passage in the tubular member under the influence of force applied against the wires by the anchor member while sliding the anchor member along the wires.

7. A method as set forth in claim 1 wherein said step of moving the anchor member along a passage in the tubular member is performed with at least a portion of the anchor member enclosed by an expansion member, said method further includes the step of expanding at least a portion of the passage in the tubular member by transmitting force from the expansion member to the tubular member while moving the expansion member and the anchor member together along the passage in the tubular member.

8. A method as set forth in claim 1 further including the steps of covering indicia on the tubular member with body tissue as the tubular member is inserted into the body tissue, and interrupting said step of inserting the tubular member into body tissue in response to covering of indicia corresponding to a desired depth of insertion of the tubular member into body tissue.

9. A method of positioning an anchor member relative to body tissue, said method comprising the steps of providing a tubular member, said step of providing a tubular member includes providing a tubular member which at least partially encloses a plurality of wires which extend along at least a portion of the passage in said tubular member, inserting the tubular member into body tissue by piercing the body tissue with an end portion of the tubular member and moving at least a portion of the tubular member through an opening formed in the body tissue by piercing the body tissue with the end portion of the tubular member, moving the anchor member along a passage in the tubular member, said step of moving the anchor member along a passage in the tubular member includes applying force against the anchor member with a pusher member and sliding the pusher member along the wires, and moving the anchor member out of the passage in the tubular member into the body tissue.

10. A method as set forth in claim 9 further including the step of expanding at least a portion of the passage in the tubular member by transmitting force from a leading end portion of the anchor member to the tubular member while moving the anchor member along the passage in the tubular member.

11. A method as set forth in claim 9 wherein said step of piercing the body tissue includes forming an opening in the body tissue at a location which is free of naturally occurring openings.

12. A method as set forth in claim 9 further including the step of expanding at least a portion of the passage in the tubular member by resiliently stretching material which forms at least a portion of the tubular member.

13. A method as set forth in claim 9 further including the step of moving segments of the end portion of tubular member which pierced the body tissue from an initial position in which portions of the segments of the end portion of the tubular member are disposed in engagement with each other to an extended position in which the portions of the segments of the end portion of the tubular member are spaced apart from each other.

14. A method as set forth in claim 9 further including the step of expanding at least a portion of the passage in the tubular member under the influence of force applied against the wires by the anchor member while sliding the anchor member along the wires.

15. A method as set forth in claim 9 wherein said step of moving the anchor member along a passage in the tubular member is performed with at least a portion of the anchor member enclosed by an expansion member, said method further includes the step of expanding at least a portion of the passage in the tubular member by transmitting force from the expansion member to the tubular member while moving the expansion member and the anchor member together along the passage in the tubular member.

16. A method as set forth in claim 9 further including the steps of covering indicia on the tubular member with body tissue as the tubular member is inserted into the body tissue, and interrupting said step of inserting the tubular member into body tissue in response to covering of indicia corresponding to a desired depth of insertion of the tubular member into body tissue.

17. A method of positioning an anchor member relative to body tissue, said method comprising the steps of providing a tubular member, inserting the tubular member into body tissue by piercing the body tissue with an end portion of the tubular member and moving at least a portion of the tubular member through an opening formed in the body tissue by piercing the body tissue with the end portion of the tubular member, moving the anchor member along a passage in the tubular member, said step of moving the anchor member along a passage in the tubular member is performed with at least a portion of the anchor member enclosed by an expansion member, expanding at least a portion of the passage in the tubular member by transmitting force from the expansion member to the tubular member while moving the expansion member and the anchor member together along the passage in the tubular member, and moving the anchor member out of the passage in the tubular member into the body tissue.

18. A method as set forth in claim 17 further including the step of expanding at least a portion of the passage in the tubular member by transmitting force from a leading end portion of the anchor member to the tubular member while moving the anchor member along the passage in the tubular member.

19. A method as set forth in claim 17 wherein said step of piercing the body tissue includes forming an opening in the body tissue at a location which is free of naturally occurring openings.

20. A method as set forth in claim 17 further including the step of expanding at least a portion of the passage in the tubular member by resiliently stretching material which forms at least a portion of the tubular member.

21. A method as set forth in claim 17 further including the step of moving segments of the end portion of tubular member which pierced the body tissue from an initial position in which portions of the segments of the end portion of the tubular member are disposed in engagement with each other to an extended position in which the portions of the segments of the end portion of the tubular member are spaced apart from each other.

22. A method as set forth in claim 17 further including the steps of covering indicia on the tubular member with body tissue as the tubular member is inserted into the body tissue, and interrupting said step of inserting the tubular member into body tissue in response to covering of indicia corresponding to a desired depth of insertion of the tubular member into body tissue.

* * * * *